United States Patent
Adams (10) Patent No.: US 11,617,693 B2
(45) Date of Patent: Apr. 4, 2023

(54) PROTECTIVE CAST COVER

(71) Applicant: Brenda Dawn Adams, Tucson, AZ (US)

(72) Inventor: Brenda Dawn Adams, Tucson, AZ (US)

( * ) Notice: Subject to any disclaimer, the term of this patent is extended or adjusted under 35 U.S.C. 154(b) by 0 days.

(21) Appl. No.: 16/907,111

(22) Filed: Jun. 19, 2020

(65) Prior Publication Data
US 2021/0038445 A1 Feb. 11, 2021

Related U.S. Application Data

(60) Provisional application No. 62/921,462, filed on Jun. 20, 2019.

(51) Int. Cl.
*A61F 15/00* (2006.01)
(52) U.S. Cl.
CPC .................................. *A61F 15/004* (2013.01)
(58) Field of Classification Search
CPC ..... A61F 15/004; A61F 13/041; A61F 13/043
USPC ........................................................... 602/3
See application file for complete search history.

(56) References Cited

U.S. PATENT DOCUMENTS

| | | | | |
|---|---|---|---|---|
| 3,329,144 A * | 7/1967 | Liman | .................... | A61F 15/004 602/3 |
| 6,126,621 A * | 10/2000 | Aceves | .................. | A61F 13/041 128/878 |
| 6,916,301 B1 * | 7/2005 | Clare | .................... | A61F 15/004 128/856 |
| 7,198,608 B2 * | 4/2007 | Wyckoff | ................ | A61F 13/041 602/3 |
| 10,568,784 B2 * | 2/2020 | Gaffney | ................ | A61F 15/004 |
| 2004/0199092 A1 * | 10/2004 | Biewend | ................ | A61F 15/004 602/3 |
| 2015/0290053 A1 * | 10/2015 | Loughney | .............. | A61F 15/004 602/3 |
| 2020/0289334 A1 * | 9/2020 | Choudhury | ............. | A61F 13/60 |

* cited by examiner

*Primary Examiner* — Keri J Nelson (57) ABSTRACT

The Protective Cast Cover is a cover you wear over your cast. It is made of fabric, any kind of fabric, waterproof, warm, breathable, what ever kind of fabric will work for an individual's needs. For arms it covers the whole arm with a mitten hand over the top of the shoulder. Some of them are shirts, just depends on what the individual request. The cover for legs covers the foot to the top of thigh and can be made as pants, or as shorts on the opposite side of the leg with the cast. If they are in double casts, then both sides would be made the same. This works for arms or legs. Again, just depends on what the individual request. The protective cast cover is meant to keep sand, or debris or even water out of the cast, and give people less stress about their situation.

9 Claims, 9 Drawing Sheets

Adjustable leg cover

A. — Soft elastic adjustable with velcro, snaps or buttons

B. Soft elastic on both sides of leg

C. Strong velcro, or elastic with snaps or buttons on both sides of leg

D. Soft elastic with velcro snaps or buttons to make adjustments

E. Solid piece of fabric from thigh down around foot

Adjustable leg cover

A. – Soft elastic adjustable with velcro, snaps or buttons

B. Soft elastic on both sides of leg

C. Strong velcro, or elastic with snaps or buttons on both sides of leg

D. Soft elastic with velcro snaps or buttons to make adjustments

E. Solid piece of fabric from thigh down around foot

Figure 1

Custom Fit Pants leg cast cover

A. Soft elastic waistband

B. Velcro and/or zipper all the way down

C. Soft elastic around ankle

D. Solid leg including foot

Custom Fit Short sleeve shirt cast cover

A. Soft elastic in mock-turtle neck

B. Velcro

C. Soft elastic around arm

D. Velcro and/or zipper

E. Soft elastic waistband

F. Full sleeve into mitten hand

Figure 4

Custom Fit no sleeve arm cast cover

A. Soft elastic mock turtle-neck

B. thinner soft elastic neck line

C. Soft elastic arm band

D. velcro and/or zipper

E. Full arm cover with mitten hand

F. Soft elastic waistband

Figure 5

Custom Fit no sleeve arm cast cover

A. Soft elastic band

B. Velcro and/or zipper

C. Full arm cover with mitten hand

D. Soft elastic waistband

Adjustable arm cast cover

A. Soft elastic

B. Soft elastic with velcr, snaps or buttons

C. Opening to pull B. elastic through to adjust it

D. Opening with velcro, snap or button to adjust A. Soft Elastic

E. Full arm cover with mitten hand

F. Elastic with snaps or buttons for adjusting on both sides of arm

PROTECTIVE CAST COVER

The protective cast cover is a soft, comfortable, washable, and can be waterproof depending on the fabric used cover for over a cast. It is one continues piece. Its purpose is to keep sand, debris, and water out of a cast. For an arm it has a mitten hand and continues all the way up over the top of the shoulder. There is elastic, an exceptionally soft elastic sewn into the top of the shoulder so that it fits snug around the shoulder. There is a soft elastic strap that crosses from the top of the shoulder across chest and back to under the opposite arm. This is all to hold it in place and not worry about it slipping down. Fits under any shirt without worry. This style can be made to be adjustable. Custom fit is always better, but to make it adjustable, you need to have an opening in the shoulder part that the elastic can come through and have Velcro on the end and also Velcro on the fabric part so that you can pull it to fit snug. It will also have to have the strap that goes around torso a strap that is there for the elastic to pull through and Velcro down the elastic to attach it to itself once it is pulled to the right fit. Also, will have a thin strap sewn at the wrist location with 3 snaps so that if it is a little long you can pull the strap to the right snap to make it the right length. This will be on both sides of wrist. The other versions for arm cast are shirt like. So it still has the mitten hand and goes all the way up to your shoulder as one solid piece, then continues around as a mock turtle neck that has thin velcro that connects the mock turtleneck around your neck and across the top of your shoulder. This will bring the rest of the bigger shirt pieces around your front and back where it will fit snug around armpit and velcro under arm down to waistband. The waistband will also have elastic inside to keep it pulled snug to your waste. It can also have a zipper under where the velcro down the side of the shirt body. Another way is to have the elastic in the top of the shirt cross the body from top of shoulder to under opposite arm and then velcro from under arm to waist band and could also have a zipper under the velcro. It will also have the elastic in the waistband. You can also make it a short sleeve version where the velcro from the neck continues down the top side of shoulder and to bottom of short sleeve. Elastic is in the bottom part of the sleeve, and velcro and possible zipper under velcro will still go from under arm to waistband. The waistband will still have elastic in it as well.

The leg cast cover is the same concept, to keep out sand, debris, and water. It will be one continuous piece of fabric that goes over the foot to the top of the thigh. There will be elastic around the top of thigh to keep it snug, and a strap of elastic from the front and back of the top going upwards towards the elastic belt. The elastic upward straps are attached to the elastic belt part that goes around the waste. This can also be made adjustable by adding snaps to the elastic belt part and the straps that are vertical. And the thigh elastic would need an opening to be able to be pulled and have velcro attached so that it can be pulled to correct fit. This cover can fit under shorts, and underwear. If you do not want to have to pull it down to use the restroom you wear it under your under garments and do not need to move it to use the restroom. If you wear it over your undergarments, then it is easy to pull the elastic waistband and straps down to use the restroom. Leg covers can also be made as a pair of shorts for on the leg without the cast. So full leg covers up to waist and around to hip all as one piece of fabric and it will velcro down the outside from waist to around the leg opening. Leg opening and waist band will both have elastic inside. This same concept is used to make them as a pair of pants. The pants are also used to keep warm by using a fleece or sweat pant material. This way when people need pants while having a broken leg and it is cold, they can actually wear pants. Really all the covers can be made from any material for any occasion. But will only be waterproof when using the waterproof fabric.

BRIEF DESCRIPTIONS

FIG. 1.

FIG. 1 of the drawings Is the adjustable leg cover. It has a soft elastic waist band with vertical elastic going from the waistband to the top of thigh fabric on both the front and the back of the leg. There is soft elastic in the top of the fabric around the thigh that is also adjustable. The leg cover is one piece of fabric that goes from top of thigh all the way down and around the foot. It can be made of any fabric that the someone would like to have including waterproof. The adjustable parts of this can be done by velcro, snaps, or buttons. Can be worn under undergarments to make using the restroom quite easy. Or it can be over undergarments and can be pulled up and down easily.

FIG. 2.

FIG. 2 of the drawings is the custom fit pants cast cover. It also has soft elastic waistband and elastic around the ankle of the un-broken foot. There is a zipper and/or strong velcro all the way down the leg of the un-broken pant leg. The other pant leg is a solid piece that goes from waist all the way down over the foot. Can be made of any material including waterproof.

FIG. 3.

FIG. 3 of the drawings is the custom fit cast cover. It has the soft elastic waistband, with the same soft elastic vertical to the top of the thigh, which also has soft elastic to keep it snug around the thigh. Then it is the one solid piece down the leg and around the foot. This to can also be made of any fabric including waterproof.

FIG. 4.

FIG. 4 of the drawings is a custom fit shirt cast cover. It has a mock turtleneck that is soft elastic and velcro from the side of the neck down the shoulder of the un-broken arm to the bottom of the short sleeve that also has elastic to keep the snug fit. It also has elastic around the waistband to keep the snug fit, and zipper and/or velcro from waistband to just under the arm pit. The other arm is a solid piece with a mitten hand. This can be made of any material including waterproof.

FIG. 5.

FIG. 5 is a custom fit shirt cast cover with no sleeve, it stops on the shoulder. It can have a regular neck or a mock turtleneck with elastic around it either way. Also, the velcro from the neck to the top of the shoulder. Also, soft elastic around the waistband to keep the snug fit. There is velcro and/or a zipper from waistband up to just under the arm pit. The other arm is one solid piece with a mitten hand. This can be made of any fabric including waterproof.

FIG. 6.

FIG. 6 of the drawings is a custom fit no sleeve shirt cast cover. It has a soft elastic that goes from the top of the shoulder of the broken room to under the other arm. It has velcro and/or zipper from the waistband to the underarm elastic. The waistband has the soft elastic for the snug fit. The sleeve on the broken arm is one solid sleeve with a mitten hand. This can be made of any material including waterproof.

FIG. 7.

FIG. 7 of the drawings is the original version of the cast cover in custom fit form. It is a solid sleeve with a mitten hand that goes all the way up the top of the shoulder with soft elastic at the top to keep it snug around the arm. It then has soft elastic that goes from the top of the sleeve across the torso to the under arm of the other arm so that it cannot slip off or down. This can be made of any fabric including waterproof.

FIG. 8.

FIG. 8 of the drawings is the original cast cover design only made adjustable. The soft elastic around the should is adjustable. The elastic that goes from shoulder across the body and under the other arm is also adjustable. The sleeve also has an elastic strap with snaps or buttons that can shorten the sleeve. It has a mitten hand. This can be made of any fabric including waterproof.

FIG. 9.

FIG. 9 of the drawings is the custom fit leg cast cover with shorts as the other leg. There is soft elastic around the waist and around the thigh of the shorts leg side. There is velcro and/or zipper from the bottom of the short to the waistband. The other leg is the full leg all the way down to covering the foot. This can be made of any fabric including waterproof.

Figure 1:
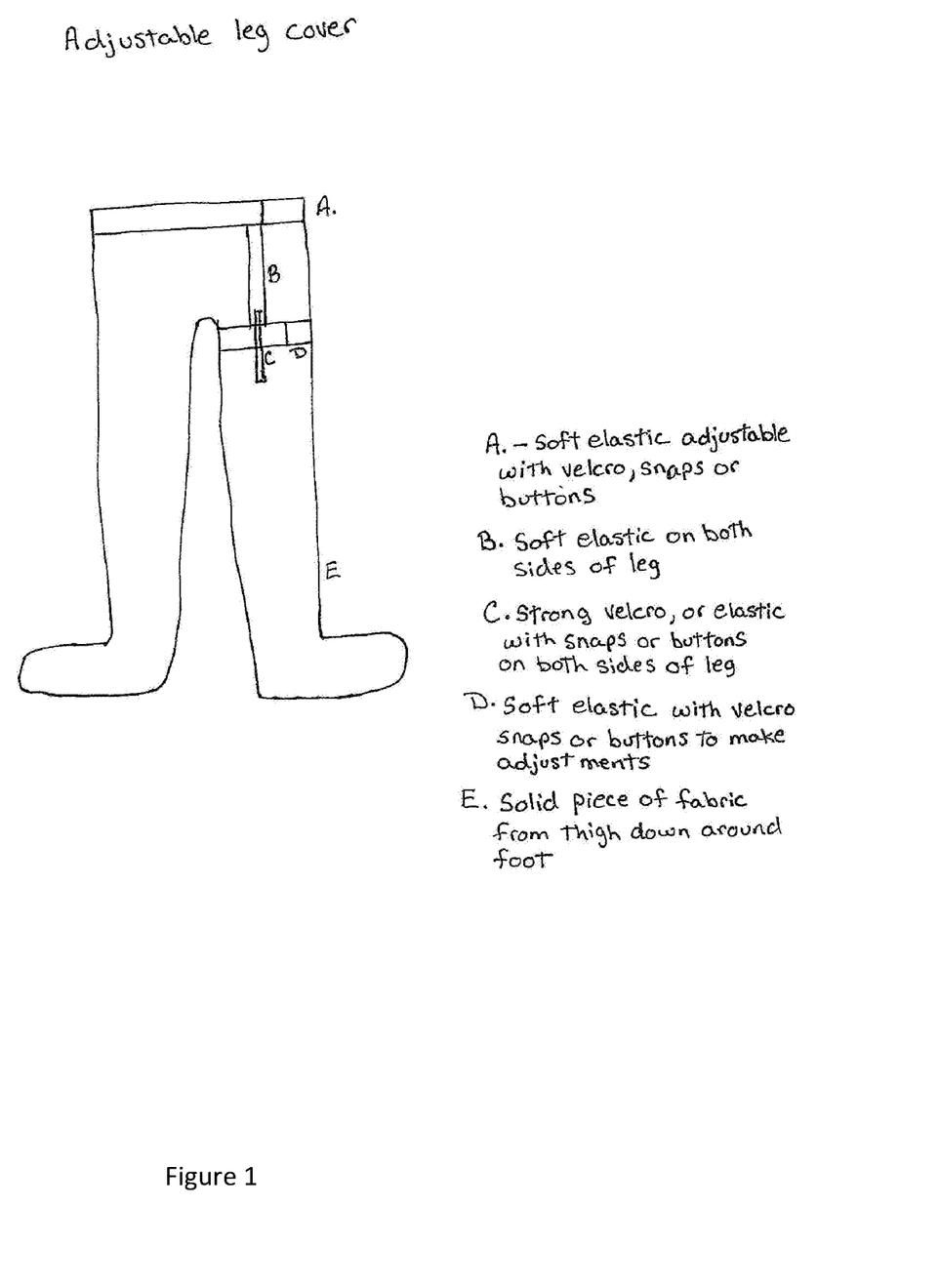
Figure 2:
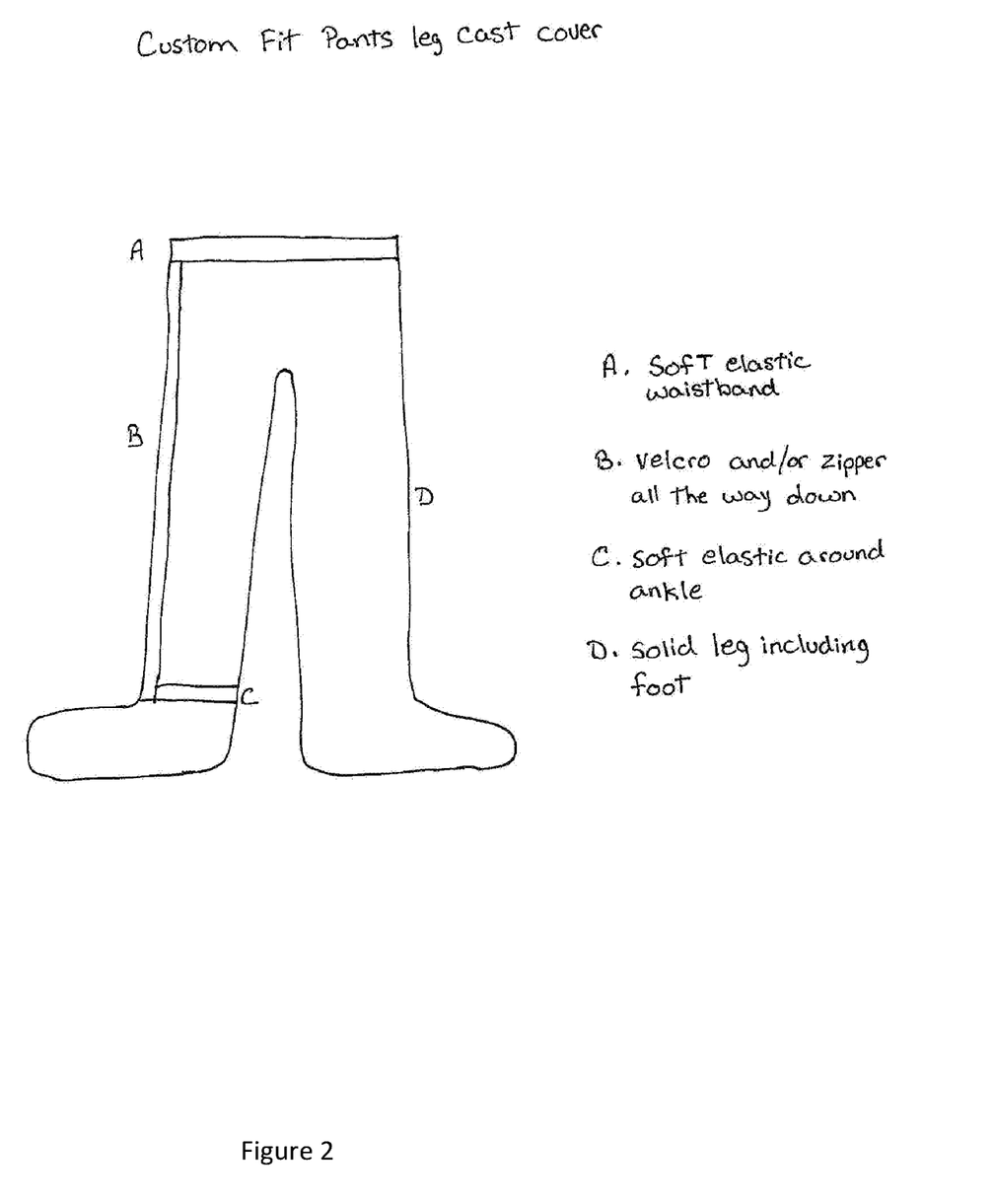
Figure 3:
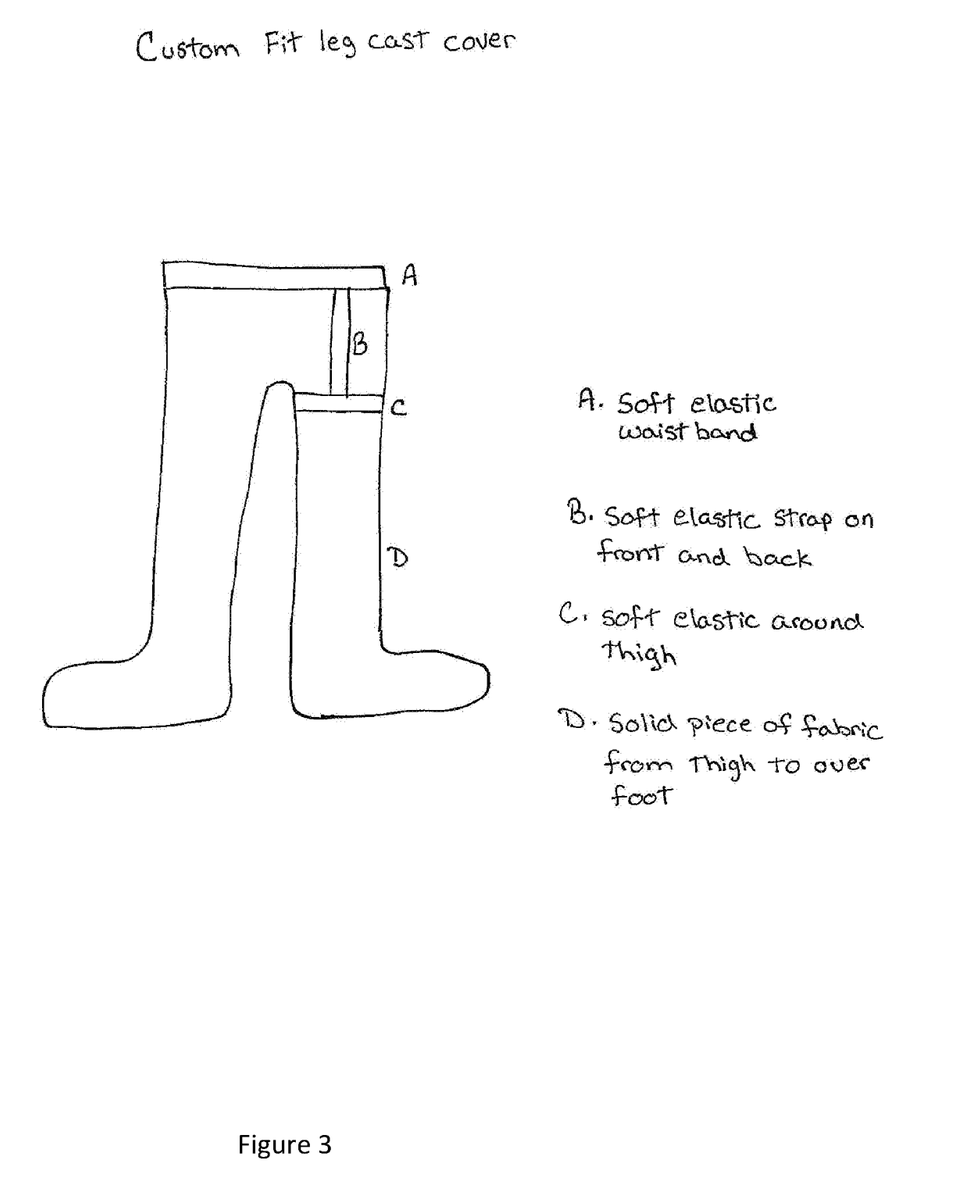
Figure 4:
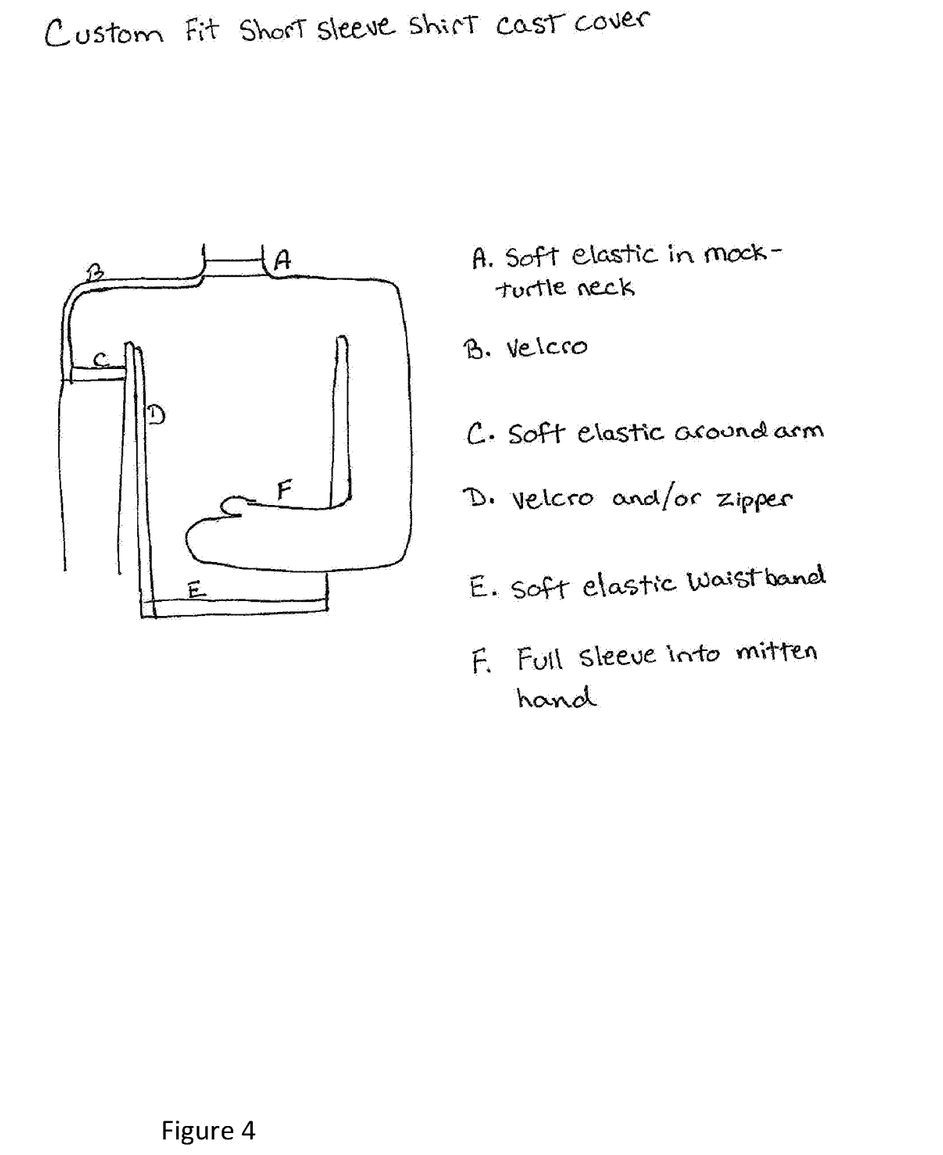
Figure 5:
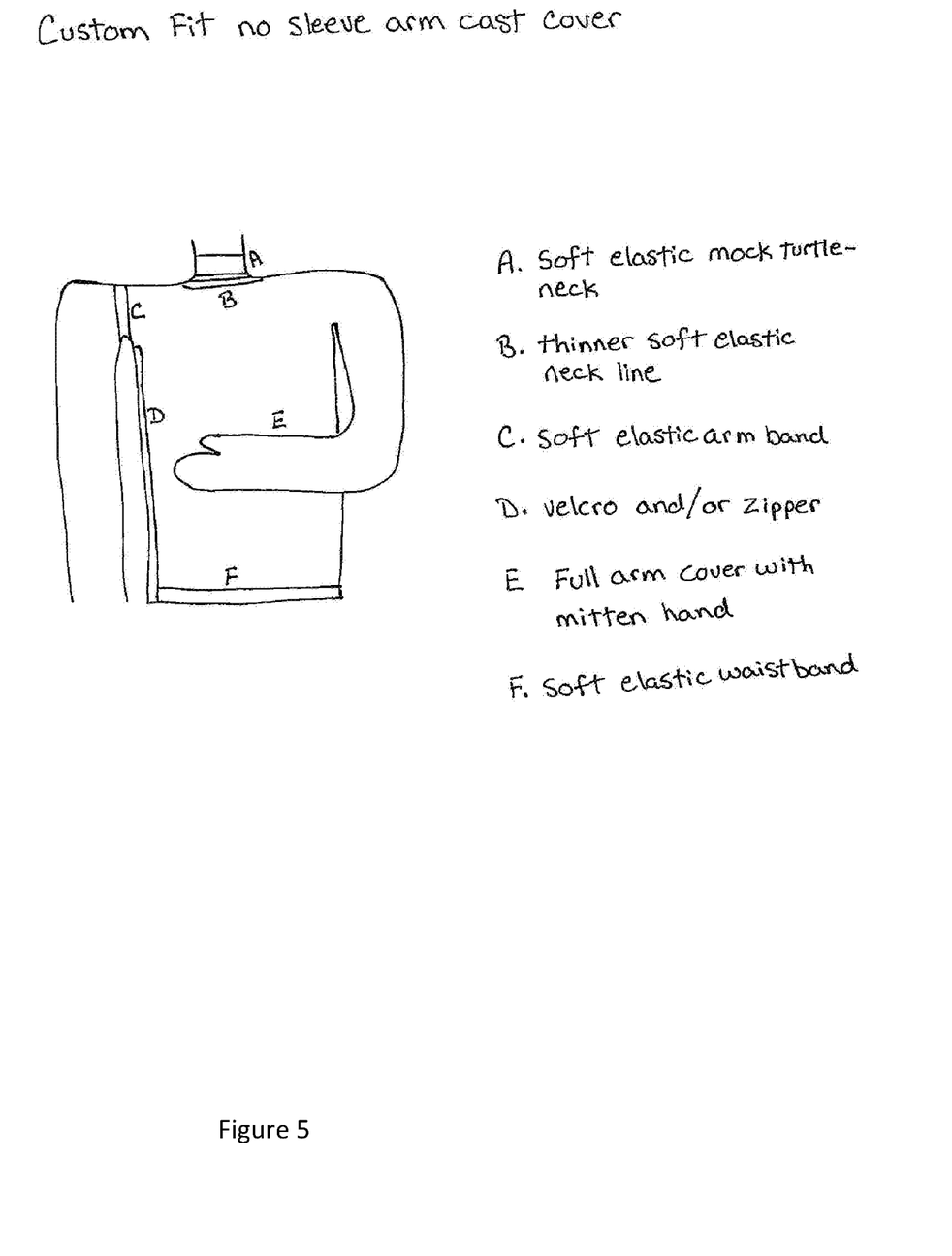
Figure 6:
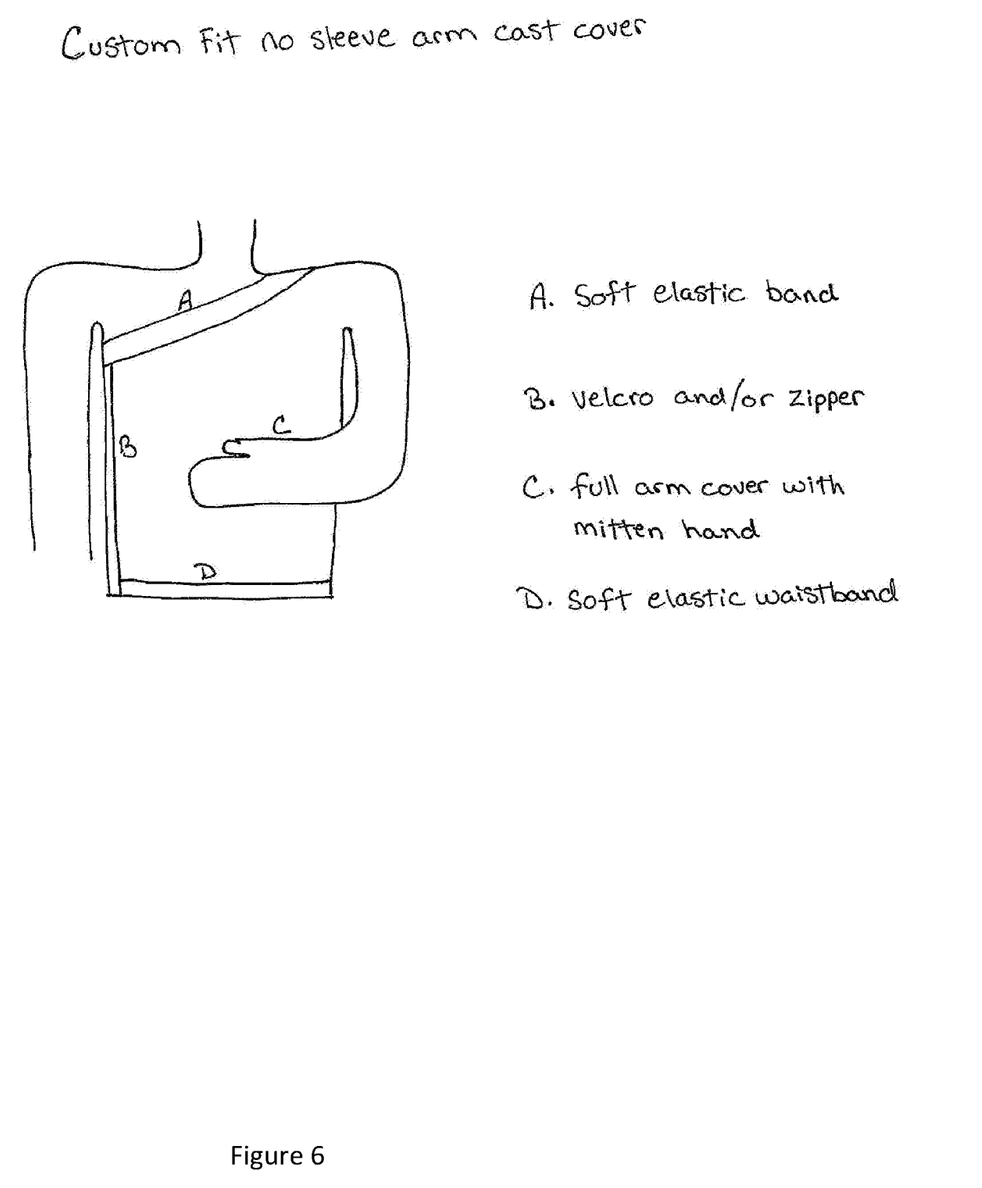
Figure 7:
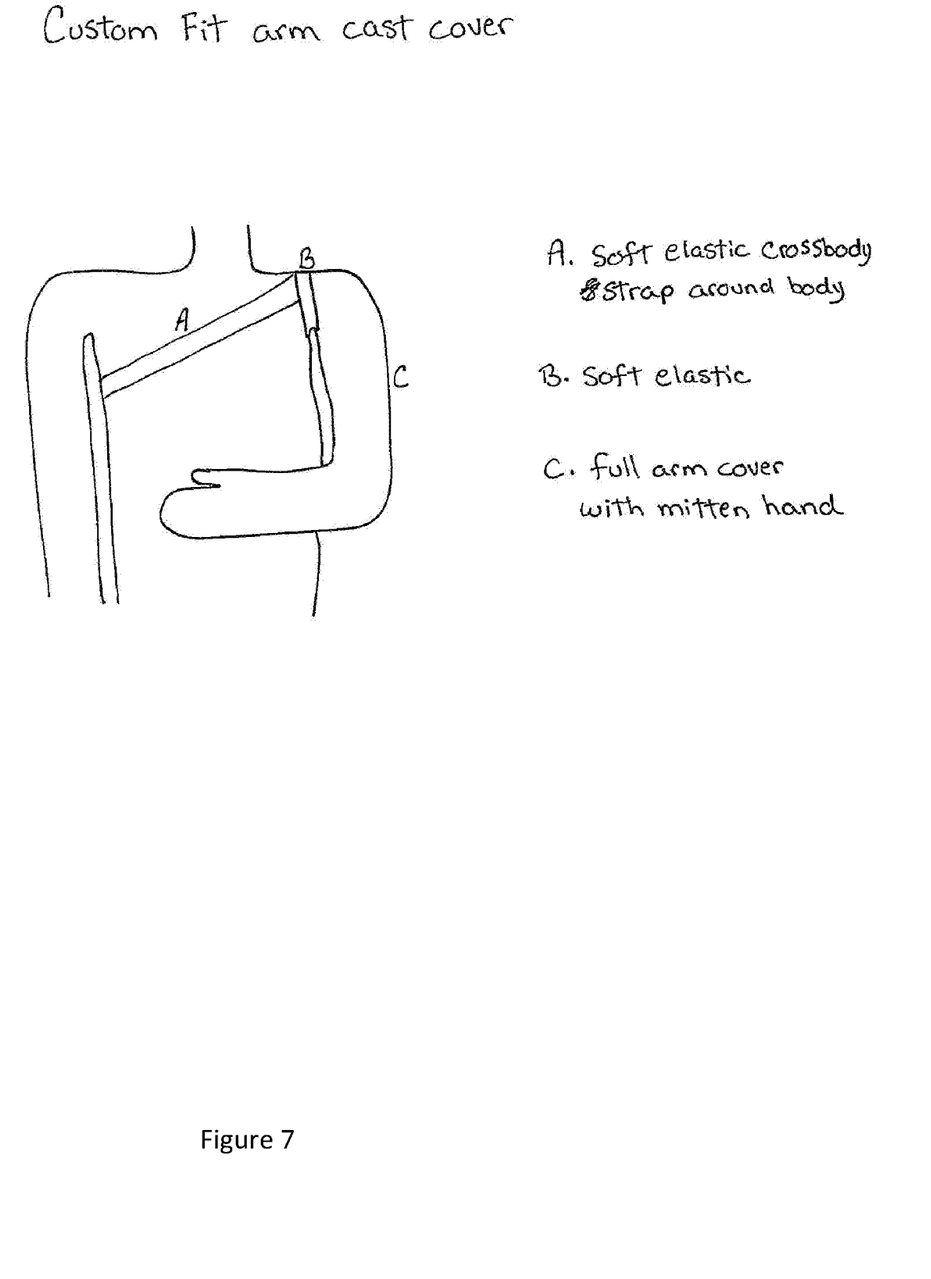
Figure 8:
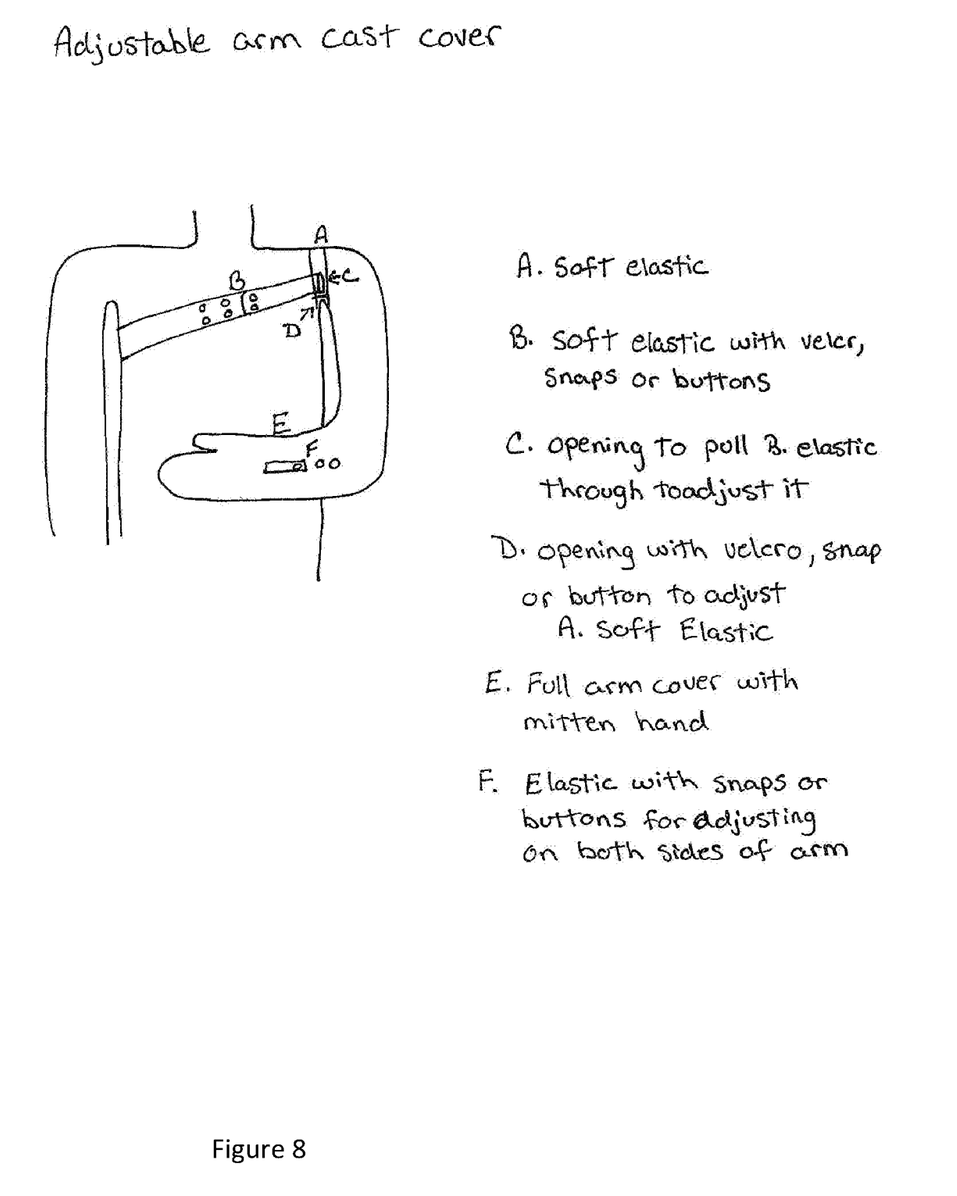
Figure 9:
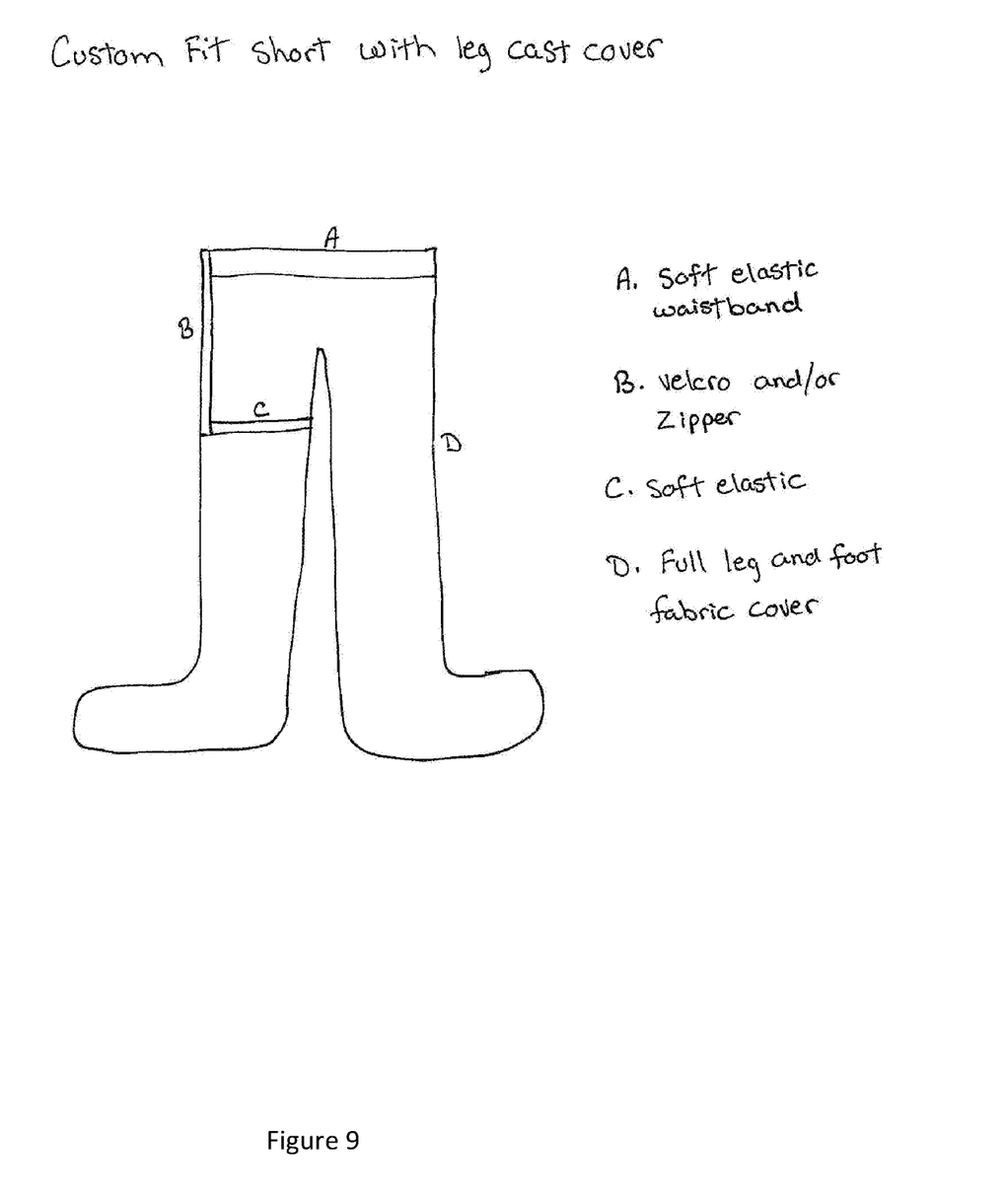

The invention claimed is:

1. A protective cast cover comprising:
 a continuous piece of waterproof fabric shaped to accommodate a user's limb and a cast worn on the limb, the fabric configured to keep out sand, debris, and water;
 the fabric forming an open proximal end configured to extend around the user's limb and a closed distal end shaped to accommodate the user's hand or foot;
 a soft elastic sewn into the fabric at the open proximal end;
 an opening formed in the fabric adjacent the soft elastic to allow the soft elastic to come through the opening;
 a first fastener secured to the soft elastic and a second fastener secured to the fabric, the first fastener and the second fastener cooperating to enable the protective cast cover to be adjusted and fit snuggly on the user's limb, wherein the first fastener and the second fastener are hook and loop closures, snaps, or buttons;
 a first strap attached to the fabric adjacent the closed distal end having a first snap;
 three snaps attached to the fabric adjacent the first strap and cooperating with the first snap to adjust a length of the protective cast cover; and
 at least one second strap attached to the fabric adjacent the open proximal end for securing the protective cast cover to the user;
 wherein the protective cast cover is washable.

2. The protective cast cover according to claim 1, wherein the fabric is configured to accommodate the user's arm, the closed distal end is shaped to accommodate the user's hand, the open proximal end is configured to fit around the user's shoulder, and the at least one second strap is configured to extend around the user's torso.

3. The protective cast cover according to claim 1, wherein the fabric is configured to accommodate the user's leg, the closed distal end is shaped to accommodate the user's foot, and the open proximal end is configured to fit around the user's upper leg, and wherein the protective cast cover further comprises an elastic waistband and the at least one second strap includes two straps configured to attach to the elastic waistband with one of the two straps attached to an anterior side of the protective cast cover and another of the two straps attached to a posterior side of the protective cast cover.

4. A protective cast cover comprising:
 a continuous piece of waterproof fabric shaped to accommodate a user's limb and a cast worn on the limb, the fabric configured to keep out sand, debris, and water;
 wherein the fabric is formed as a garment including a closed end, a first opening, and a second opening having an elastic waistband;
 wherein the garment is configured to accommodate the user's torso or legs and the closed end is shaped to accommodate the user's hand or foot;
 a soft elastic sewn into the fabric at the first opening; and
 a fastener extending from the first opening to the second opening, wherein the fastener is a zipper, a hook and loop closure, or a combination thereof;
 wherein the protective cast cover is washable.

5. The protective cast cover according to claim 4, wherein the garment is configured to cover a first arm of the user and the first opening is configured to extend around the user's neck and/or a second arm of the user.

6. The protective cast cover according to claim 4, wherein the garment is configured to cover a first leg of the user and the first opening is configured to extend around a second leg of the user.

7. A custom protective cast cover comprising:
 a continuous piece of waterproof fabric custom made to accommodate a user's limb and a cast worn on the limb, the fabric configured to keep out sand, debris, and water;
 wherein the fabric is formed as a garment including a closed end, a first opening, and a second opening having an elastic waistband;
 wherein the garment is configured to accommodate the user's torso or legs and the closed end is shaped to accommodate the user's hand or foot;
 a soft elastic sewn into the fabric at the first opening; and
 a fastener extending from the first opening to the second opening, wherein the fastener is a zipper, a hook and loop closure, or a combination thereof;
 wherein the protective cast cover is washable.

8. The custom protective cast cover according to claim 7, wherein the garment is configured to cover a first arm of the user and the first opening is configured to extend around the user's neck and/or a second arm of the user.

9. The custom protective cast cover according to claim 7, wherein the garment is configured to cover a first leg of the user and the first opening is configured to extend around a second leg of the user.

* * * * *